(12) United States Patent
Goel

(10) Patent No.: US 8,247,398 B2
(45) Date of Patent: Aug. 21, 2012

(54) ZINC COMPLEXES OF NATURAL AMINO ACIDS FOR TREATING ELEVATED COPPER CAUSED TOXICITIES

(75) Inventor: Om P. Goel, Ann Arbor, MI (US)

(73) Assignee: SSV Therapeutics, Inc., Ann Arbor, MI (US)

( * ) Notice: Subject to any disclaimer, the term of this patent is extended or adjusted under 35 U.S.C. 154(b) by 1272 days.

(21) Appl. No.: 11/707,329

(22) Filed: Feb. 17, 2007

(65) Prior Publication Data

US 2008/0200443 A1 Aug. 21, 2008

(51) Int. Cl.
*A01N 55/02* (2006.01)
*A01N 43/76* (2006.01)
*A61K 31/41* (2006.01)

(52) U.S. Cl. ......... 514/184; 514/186; 514/360; 514/375
(58) Field of Classification Search ............... 514/184, 514/186, 360, 375
See application file for complete search history.

(56) References Cited

U.S. PATENT DOCUMENTS

| | | | |
|---|---|---|---|
| 4,167,564 | A | 9/1979 | Jensen |
| 4,599,152 | A | 7/1986 | Ashmead |
| 5,582,817 | A | 12/1996 | Otsu et al. |
| 6,359,007 | B1 | 3/2002 | Pearson et al. |
| 6,855,340 | B2 | 2/2005 | Brewer |
| 2007/0207191 | A1* | 9/2007 | Kanzer et al. ............... 424/449 |

OTHER PUBLICATIONS

Brewer, George J, MD; Wilson's Disease, a Clinician's Guide to Recognition, Diagnosis and Management; Kluwer Acad. Pub., 2001; title pg, pp. 49-59, 167-178.
Hoogenraad, T. U. et al.; J. of the Neurological Sci., 77, pp. 137-146 (1987).
Coyle, P. et al.; Cellular and Molecular Life Sciences, 59, pp. 627-647 (2002).
Cotton, A. et al.; Advanced Inorganic Chemistry, Sixth Ed., J. Wiley Pub., 1999; title pg, pp. 628-629.
Clarke, E. R. And Martell, A. E.; J. Inorg. Nucl. Chem., 32, pp. 911-926 (1970).
Rombach, M. et al.; Inorganica Chimica Acta, 334, pp. 25-33 (2002).

* cited by examiner

*Primary Examiner* — Renee Claytor
(74) *Attorney, Agent, or Firm* — Technology Law, PLLC; Karen L. Kimble

(57) ABSTRACT

The present invention relates to the use of zinc complexes of natural amino acids, especially L-arginine, L-lysine, L-ornithine, and other natural amino acids, in a molar ratio of about 1:2 (metal:amino acid), and formulations thereof. These pharmaceutical compositions offer better tolerated and faster acting regimens than common zinc salts (i.e., acetate, sulfate, etc.) for long term maintenance therapy of diseases caused by abnormal elevated copper levels, such as in Wilson's disease, inflammatory and fibrotic diseases and Alzheimer's disease.

9 Claims, No Drawings

ZINC COMPLEXES OF NATURAL AMINO ACIDS FOR TREATING ELEVATED COPPER CAUSED TOXICITIES

BACKGROUND OF THE INVENTION

1. Field of the Invention

The invention encompasses the clinical uses of zinc complexes of natural amino acids, such as those natural amino acids with basic side chains, for example L-arginine, lysine, ornithine, and histidine, and other alpha amino acids of natural occurrence, in treating elevated copper caused toxicities, in the maintenance therapy of Wilson's disease, and also in combination with other copper binding drugs, like penicillamine, trientine and thiomolybdates. These zinc complexes may similarly be used to treat inflammatory and fibrotic diseases such as pulmonary fibrosis, liver cirrhosis, hepatitis C, kidney disease, and Alzheimer's disease.

2. Description of Related Art

Zinc salts (acetate or sulfate) are anti-copper agents used in the lifetime management of Wilson's disease, which is an inherited disorder and causes abnormal copper accumulation in the body. This copper accumulation causes severe toxicity in the liver, brain and other vital organs of its afflicted patients. Its onset is at a relatively young age, and is fatal, if not diagnosed early and treated correctly. (See *Wilson's Disease, A Clinician's Guide to Recognition, Diagnosis, and Management*, George J. Brewer; Kluwer Academic Publishers, 2001, and references cited therein.) For fast lowering of dangerous copper levels, patients may be acutely treated with either: the potent, yet toxic, classical copper binding drugs like penicillamine or trientine; or the safer tetrathiomolybdates, in addition to customary zinc salts (acetate or sulfate). For maintaining essential copper homeostasis, patients are treated to lifetime therapy of non-toxic zinc salts. (For example, as taught in U.S. Pat. No. 6,855,340.)

$Zinc^{+2}$ dicationic species exerts its biological effect by inducing the upregulation of the zinc and/or cadmium containing metallothioneins' production in the intestinal cell wall, liver and other tissues [e.g., Induction, Regulation, Degradation, and Biological Significance of Mammalian Metallothioneins; A. T. Miles, G. M. Hawksworth, J. H. Beattie and V. Rodilla; *Critical Reviews in Biochemistry and Molecular Biology*, 35 (1), 35-70 (January-February 2000); and Metallothionein: the multipurpose protein, P. Coyle, J. C. Philcox, L. C. Carey, and A. M. Rofe; *Cellular and Molecular Life Sciences*, 59(4), 627-647 (April 2002)]. Metallothioneins are a 61-62 amino acid protein, about a third of which amino acids are cysteines, strongly bind copper, cadmium, and mercury in the food, saliva, and gastrointestinal secretions, preventing their transfer into the blood (see *Advanced Inorganic Chemistry*, Sixth Edition, F. Albert Cotton, G. Wilkinson, C. Murillo, M. Bochmann, J. Wiley $ Sons, New York, 1999, pp. 628-629). The resulting protein-complexed copper is eliminated in the stool.

Zinc acetate (Galzin®) is approved by the U.S. FDA (1997) for Wilson's disease maintenance therapy in capsules containing 25 or 50 mg of equivalents of zinc, taken three times daily (t.i.d). In some patients, zinc acetate causes gastric irritation and discomfort, which is believed due to it's conversion into zinc chloride in the strongly acidic stomach. About 10% of the patients receiving zinc acetate therapy encounter persistent gastric irritation, burning sensation, and nausea, causing critical patient compliance issues (George J. Brewer in *Wilson's Disease, A Clinician's Guide to Recognition, Diagnosis, and Management*, George J. Brewer; Kluwer Academic Publishers, 2001, pp. 55-56).

Zinc sulfate is also used, but it causes even more patient discomfort (Hoogenraad T U. Wilson's Disease. In: Warlow C P, Van Gijn., J. Eds., *Major problems in Neurology* Vol. 30, London: W.B. Saunders Co. 1996).

The initial undesirable effects of zinc salts are exacerbated as the drug is taken on an empty stomach or in-between meals. Usually it takes several days or weeks before zinc acetate therapy is tolerable to the patient (*Wilson's Disease, A Clinician's Guide to Recognition, Diagnosis, and Management*, George J. Brewer; Kluwer Academic Publishers, 2001, p. 57).

Complexes of arginine and bisarginine with $Mg^{+2}$, $Cu^{+2}$, and $Zn^{+2}$ are reported to be useful in ameliorating chronic essential hypertension, cerebral vascular disease, glaucoma, wound healing, acute and chronic inflammation, and Alzheimer's disease (see U.S. Pat. No. 6,359,007).

Therefore, an alternative form of zinc delivery without the gastric side-effects would be beneficial to patients of Wilson's disease, and in other diseases requiring safe, long-term prevention of copper accumulation and resulting toxicities.

BRIEF SUMMARY OF THE INVENTION

This invention concerns zinc amino acid complexes or zinc chelates of amino acids, as soothing, better tolerated agents than common zinc salts, in controlling long-term, elevated copper levels in Wilson's disease patients, and in other inflammatory, and fibrotic diseases, and Alzheimer's disease. Additionally, these zinc amino acid complexes are used as a method of inducing metallothionein production in various organs and tissues in the animal or human body. Pharmaceutically-acceptable compositions of these complexes are also included, optionally with added active components and/or pharmaceutically-acceptable carriers and additives for use.

Specifically, a method for the treatment of elevated copper caused toxicities in an animal or human which comprises administrating to the animal or human in need of such treatment a pharmaceutically-acceptable, effective amount of a composition comprising a complex of the formula

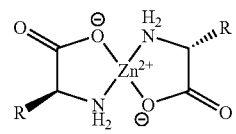

Formula I wherein R is derived from synthetic or naturally occurring amino acid moiety and may be the same or different R group; the ratio of the zinc to the amino acid moiety is 1:2; and the complex is substantially free of external ions.

DETAILED DESCRIPTION OF THE INVENTION

Glossary

The following terms as used in this application are to be defined as stated below and for these terms, the singular includes the plural.

GI means gastrointestinal use or contact
NF means National Formulary
t.i.d. means three times a day
V blender means a V-shaped blender used for mixing solid powders by tumbling action such as that made by Paul O. Abbe (Totowa, N.J.)
Zinc Compounds/Zinc Complexes of this Invention The purpose of this invention is to provide zinc amino acid complexes or zinc chelates of amino acids, as soothing, better tolerated agents than common zinc salts, in controlling long-term, elevated copper levels in Wilson's disease patients, and in other inflammatory, and fibrotic diseases, and Alzheimer's disease. Although any amino acid can be used to complex with zinc, the natural amino acids are preferred. In particular, zinc complexes of natural alpha amino acids with basic side-chains, such as with arginine, lysine, histidine, and ornithine are preferred, as these are very stable in the low pH environment of the stomach, and have the additional benefit of counteracting stomach acidity via acid-base neutralization. Arginine and lysine are constituents of mammalian metallothioneins to the extent of ~1 and 7 units respectively, per metallothionein molecule. Glycine (no side-chain) is present as a constituent of mammalian metallothioneins at ~5 units/metallothionein. Significantly, there is none of the aromatic amino acids or histidine present in metallothioneins.

Zinc arginate, with it's strongly basic guanidine side-chain and substantial proton affinity, is expected to be particularly less irritating, better tolerated, and accepted by the patient, obviating the initial compliance problems [see Metal Chelates of Arginine and Related Ligands; E. R. Clarke and A. E. Martell, *J. Inorganic and Nuclear Chemistry*, 32, 911-926 (1970)]. The need to prepare and test enteric formulations is also avoided.

Mixtures of zinc arginate, zinc lysinate and/or zinc glycinate may also be used. Especially significant is that zinc-amino acids complexes have the effect of inducing metallothionein production in various tissues (see U.S. Pat. No. 5,582,817).

Interestingly, although histidine is not a constituent of metallothioneins, oral administration of it's zinc chelate strongly induced metallothionein production in male Wistar rat livers within 12 hours (14-39 fold over control group), (see U.S. Pat. No. 5,582,817). Higher levels of hepatic metallothionein are of great significance in treatment of Wilson's disease, as this will safely sequester and remove hepatic copper providing faster relief from hepatic copper toxicity (*Wilson's Disease, A Clinician's Guide to Recognition, Diagnosis, and Management*, George J. Brewer; Kluwer Academic Publishers, 2001, p. 52). Zinc dipicolinate in the same test, substantially raised metallothionein induction in the epidermis, sebaceous glands and hair follicles. The zinc arginine/lysine/histidine/ornithine type of amino acid complexes are expected to demonstrate dual benefits of better GI tolerance, and potentiated metallothionein induction in various tissues, leading to faster onset of action in preventing copper absorption from food and gastric secretions, and would be a preferred method of long term maintenance therapy than the use of simple zinc salts alone. In addition, substantial and fast metallothionein induction in the liver, as demonstrated in rats, by administration of zinc histidine, would help remove excess toxic copper from this organ as well, further enhancing the therapeutic value of the amino acid complexes in diseases caused by elevated copper levels.

The present invention provides compounds as zinc complexes in which zinc is chelated with any amino acids, either synthetic or natural amino acid. In particular zinc is complexed with a basic side-chain amino acid, especially with arginine, lysine, histidine and ornithine, in the ratio of 1:2 ($zinc^{2+}$: amino acids), with no outside anions present. The zinc complex has the following structural formula and is prepared by the following reaction:

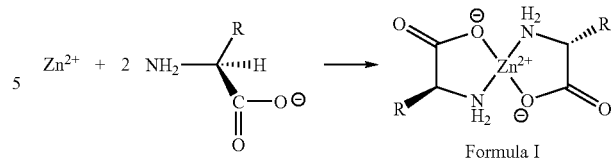

Formula I

The R group of the amino acid can be any suitable moiety that is pharmaceutically-acceptable to animals; namely, those moieties derived from synthetic or naturally occurring amino acid moieties. The preferred R groups have a basic side-chain to increase stability in the acid of the stomach. Some amino acids that can be use in Formula I are:

TABLE 1

| Amino Acid | Amino Acid Symbol | R group |
|---|---|---|
| Alanine | A or Ala | —$CH_3$ |
| Aspartic Acid | D or Asp | —$CH_2$—C(=O)—OH |
| Citrulline | | —$CH_2$—$CH_2$—$CH_2$—NH—C(=O)—$NH_2$ |
| Glutamine | Q or Gln | —$CH_2$—$CH_2$—C(=O)—$NH_2$ |
| Glutamic Acid | E or Glu | —$CH_2$—$CH_2$—C(=O)—OH |
| Glycine | G or Gly | —H |
| Histidine | H or His | —$CH_2$—(imidazole) |
| Leucine | L or Leu | —$CH_2$—CH($CH_3$)$_2$ |
| Lysine | K or Lys | —$CH_2$—$CH_2$—$CH_2$—$CH_2$—$NH_2$ |
| Methionine | M or Met | —$CH_2$—$CH_2$—S—$CH_3$ |
| Ornithine | | —$CH_2$—$CH_2$—$CH_2$—$NH_2$ |
| Phenylalanine | F or Phe | —$CH_2$—(phenyl) |
| Proline | P or Pro | (pyrrolidine-2-carboxylic acid) |
| Serine | S or Ser | —$CH_2$—OH |
| Threonine | T or Thr | —CH(OH)—$CH_3$ |

TABLE 1-continued

| Amino Acid | Amino Acid Symbol | R group |
|---|---|---|
| Tryptophan | W or Trp | —CH₂—(indole with NH) |
| Tyrosine | Y or Tyr | —CH₂—(phenyl)—OH |
| Valine | V or Val | —CH(CH₃)₂ |

The amino acids shown in Table 1 are of L-(S)-configuration, and the zinc complexes of Formula I are charge balanced, free of external inorganic anion radicals. The bidentated $Zn^{++}$ ions are tetrahedrally coordinated with the carboxylate anions and amine groups of two amino acid residues. The amino acids may also be of D- or DL-configuration.

The complexes of Formula I are not limited to just the amino acids shown in Table 1 above. Thus, any known or novel, synthetic or naturally occurring amino acid that is capable of forming a stable zinc complex (but not including a zinc salt thereof) may be used. Examples of such zinc complexes are, zinc dipicolinate, or zinc complexes of unsubstituted or 3-, 5-alkyl or alkoxy substituted pyridine-2-carboxylic acids (e.g., U.S. Pat. No. 5,582,817), zinc complexes of β-alanine, α-aminobutyric acid, α,γ-diaminobutyric acid, and canavanine (a guanidino α-amino acid from soybeans). Components of collagen, such as 4-hydroxyproline, and hydroxylysine (2,6-diamino-5-hydroxyhexanoic acid) may also be used as zinc complexes [e.g., Brinckmann, J., et al., Collagen, Topics in Current Chemistry, p 247, Springer, Berlin (2005)]. Also significant are zinc complexes of unsubstituted, and 3,4-disubstituted alkyl or alkoxy 1,2,3,4-tetrahydroisoquinolines. The latter are components of pharmaceutical agents, e.g. in quinapril (see Merck Index, 12th Ed. 8233).

The preparation of pure amino acid chelates of Formula I, such as zinc bis(L-arginate), is described in the following references: Coordination Modes of Amino Acids to Zinc; M. Rombach, M. Gelinsky, H. Vahrenkamp; *Inorganica Chimica Acta*, 334, 25-33 (2002); Metal Chelates of Arginine and Related Ligands, *J. Inorg. Nucl. Chem.*, 32, 911-926 (1970); *Chem. Comm.*, 9, 1090-1091 (2003); U.S. Pat. No. 4,599, 152). These compounds can also be purchased from Spectrum Chemicals and Lab Products, Gardena, Calif.

It is possible to contemplate, synthesize, and use mixed amino acid complexes of Formula I where zinc is complexed with different R groups, e.g., arginine-lysine, arginine-glycine, or arginine-leucine or lysine-leucine [see Zeolite Encapsulated Copper (II) Amino Acid Complexes: Synthesis, Spectroscopy and Catalysis; Weckhuysen, Bert M; Verberckmoes, An A.; Schronheydt, Robert A; *J. of Phys. Chem.* 100(22), 9456-9461 (1996)]. However, there is no practical advantage to this mixed amino acid strategy, as the complexes are more difficult to synthesize in high purity. Thus, one zinc dication complexed with two identical amino acid carboxylate anion molecules is preferred.

However, mixtures of two or more zinc-amino acid complexes of Formula I may be used. Mixtures of zinc arginate and glycinate are marketed as nutritional zinc supplements. These compositions have molecular weights of under 500 (zinc bisarginate is 412.2), which is preferred for oral absorption.

These complexes for Formula I upon oral ingestion are better tolerated than the common zinc salts. These complexes have high stability constants in the low pH acid stomach (see Metal chelates of Arginine and Related Ligands; E. R. Clarke and A. E. Martell, *J. Inorg. And Nucl. Chem.*, 32, p 911 (1970); U.S. Pat. No. 4,167,564; Jensen Ned L; *Intestinal Absorption of Metal Ions, and Chelates*, Ashmead, Graft and Ashmead; Charles C. Thomas: Publisher, Springfield, Ill., 1985). These complexes of Formula I pass mostly intact into the small intestine via active dipeptide transport where they effectively induce metallothionein production, which irreversibly binds copper from food, saliva, and gastric secretions, rendering it harmless. A fraction of the complex enters general circulation and reaches tissues such as liver where it promotes build up of needed plasma proteins such as metallothioneins. This effect is useful in the long term control of elevated copper levels related toxicities in Wilson's disease, liver inflammatory and fibrotic diseases, and in Alzheimer's disease.

Formulations of Zinc Complexes

The pharmaceutical compositions of zinc amino acid complexes may also contain physiologically-acceptable diluents, excipients, carriers, adjuvants, and the like. The phrase "pharmaceutically-acceptable" means those formulations which are, within the scope of sound medical judgment, suitable for use in contact with the tissues of humans and animals without undue toxicity, irritation, hypersensitivity/allergic response and the like, and are commensurate with a reasonable benefit/risk ratio.

The pharmaceutical compositions of this invention can be administered to humans and other mammals in a variety of ways, especially orally in a solid, or liquid form. These compositions have molecular weights of under 500 (zinc bisarginate is 412.2), which is preferred for oral absorption. Thus, a therapeutically equivalent dose of zinc bisarginate for administration in Wilson's disease patients would be about 50 to about 200 mg t.i.d., based on the current recommended dose level of zinc acetate dihydrate. Actual dosage levels of the active ingredients in the pharmaceutical formulation can be varied so as to achieve the desired therapeutic response for a particular patient.

The complexes of the present invention may also be administered in combination with other drugs, if deemed medically necessary or beneficial.

Examples of suitable aqueous and nonaqueous carriers, diluents, solvents or vehicles for use with these complexes include water, ethanol, polyols (propylene glycol, polyethyleneglycol, glycerol, and the like), vegetable oils (such as olive oil), injectable organic esters such as ethyl oleate, and suitable mixtures thereof. These compositions can also contain adjuvants such as preserving, wetting, emulsifying, and dispensing agents.

Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like.

Suspensions, in addition to the active compounds, may contain suspending agents, as for example, ethoxylated isostearyl alcohols, polyoxyethylene sorbitan esters, microcrystalline cellulose, aluminum metahydroxide, bentonite, agar-agar and tragacanth, or mixtures of these substances, and the like. Proper fluidity can be maintained, for example, by the use of coating materials such as lecithin, by the maintenance of the required particle size in the case of dispersions, and by the use of surfactants.

Liquid dosage forms for oral administration of these complexes include pharmaceutically-acceptable emulsions, solutions, suspensions, syrups and elixirs. In addition to the active complexes, and when desired other active components, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral suspending agents, sweetening, flavoring, coloring, and perfuming agents may be added.

Solid dosage forms for oral administration include capsules, tablets, pills, powders and granules, lozenges, lollipops, and other similar forms. In such solid dosage forms, the active compound may be mixed with at least one inert, pharmaceutically-acceptable excipient or carrier, such as sodium citrate or dicalcium phosphate and/or one or more of:

a) flavoring agents such as orange, cherry and others;
b) fillers or extenders such as starches, lactose, sucrose, glucose, mannitol, and silicic acid;
c) binders such as carboxymethylcellulose, alginates, gelatin, polyvinylpyrrolidone, sucrose and acacia;
d) humectants such as glycerol;
e) disintegrating agents such as agar-agar, calcium carbonate, potato or tapioca starch, alginic acid, certain silicates and sodium carbonate;
f) absorption accelerators such as quaternary ammonium compounds;
g) wetting agents such as cetyl alcohol and glycerol monostearate;
h) absorbents such as kaolin and bentonite clay; and
i) lubricants such as talc, calcium stearate, magnesium stearate, solid polyethylene glycols, sodium lauryl sulfate and mixtures thereof.

In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and similar compounds.

EXAMPLES

The invention will be further clarified by a consideration of the following examples, which are intended to be purely exemplary of the present invention.

Example 1

Capsule Formulation of Zinc Bisarginate

A mixture having 25 g of zinc bisarginate (15-16% zinc by wt.), and 250 g of anhydrous lactose NF, and 0.5 g of magnesium stearate is thoroughly mixed in a V blender for 15-30 minutes. The powder is hand-filled in #2 or larger capsules providing each capsule contains 50 mg of zinc bisarginate.

Example 2

Capsule Formulation of Zinc Bisarginate

A mixture having 50 g of zinc bisarginate and 225 g of anhydrous lactose NF, and 0.5 g of magnesium stearate is thoroughly mixed in a V blender for 15-30 minutes. The powder is hand-filled in #2 or larger capsules providing each capsule contains 100 mg of zinc bisarginate.

Example 3

Capsule Formulations of Mixed Zinc Complexes

Mixtures of 25 g or 50 g containing varying proportions of zinc bisarginate with zinc bislysinate, or zinc histidinate, and 250 g or 225 g of anhydrous lactose NF, and 0.5 g of magnesium stearate are thoroughly mixed in a V blender for 15-30 minutes. The powder is hand-filled in #2 or larger capsules to provide about 50 mg or 100 mg of the zinc-amino acid complex per capsule.

Example 4

Capsule Formulations of Mixed Zinc Complexes

Mixtures of 25 g or 50 g containing varying proportions of zinc bisarginate and zinc bisglycinate, and 250 g or 225 g of anhydrous lactose NF, and 0.5 g of magnesium stearate are thoroughly mixed in a V blender for 15-30 minutes. The powder is hand-filled in #2 or larger capsules to provide about 50 mg or 100 mg of mixed zinc-amino acid complex per capsule Example 5

Liquid Formulation of Zinc Bisarginate

Zinc bisarginate (25 g) is stirred in 450 mL of purified water, and suitable flavors like orange or cherry, with high fructose corn syrup, glycerin, sodium benzoate, red dye no. 28 (or no. 40) are added to the mixture. The water volume is adjusted to 500 mL to yield 50 mg of active zinc arginate per 5 mL (tsp).

Example 6

Liquid Formulations of Zinc Arginate, Zinc Lysinate, Zinc Histidinate, or Zinc Glycinate When the above procedure of Example 5 is repeated, syrups containing varying proportions of zinc arginate, zinc lysinate, zinc histidinate, or zinc glycinate are prepared.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

What is claimed is:

1. A method for the treatment of elevated copper caused toxicities by Wilson's disease, inflammatory and/or a fibrotic disease in an animal or human which comprises administrating to the animal or human in need of such treatment a pharmaceutically-acceptable, effective amount of a composition, consisting essentially of a complex of the formula

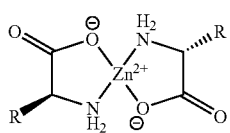

Formula I wherein R is derived from a synthetic or naturally occurring amino acid moiety selected from the group consisting of glycine, arginine, lysine, histidine and ornithine and may be the same or different R group:

the ratio of the zinc to the amino acid moiety is 1:2; and the complex is substantially free of external ions, and substantially stable in the low pH environment of the stomach.

2. The method of claim 1 where both R groups are the same.

3. The method of claim 1 wherein the R group is derived from glycine, arginine, or histidine.

4. The method of claim 3 wherein one complex of Formula I is combined with another different complex of Formula I to form an admixture in varying proportions.

5. The method of claim 4 where a zinc glycinate complex of Formula I is combined with a zinc histidinate or zinc argininate complex of Formula I as an admixture in varying proportions.

6. The method of claim 1 wherein the fibrotic disease is pulmonary fibrosis, liver cirrhosis, hepatitis C, kidney disease or Alzheimer's disease.

7. The method of claim 1 or 6 wherein the effective amount of the complex administered is from about 50 to about 200 mg three times per day.

8. The method of claim 5 where a zinc glycinate complex of Formula I is combined with a zinc histidine complex of Formula I as an admixture.

9. The method of claim 1 where both R groups are derived from a naturally occurring amino acid moiety such that both R groups are either in the S- or L-configuration.

* * * * *